US00PP25558P2

(12) United States Plant Patent
Leue

(10) Patent No.: US PP25,558 P2
(45) Date of Patent: May 12, 2015

(54) ***ANGELONIA* PLANT NAMED 'BALANGSPARKL'**

(50) Latin Name: *Angelonia angustifolia*
Varietal Denomination: Balangsparkl

(71) Applicant: Ball Horticultural Company, West Chicago, IL (US)

(72) Inventor: Ellen Leue, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 173 days.

(21) Appl. No.: 13/986,975

(22) Filed: Jun. 20, 2013

(51) Int. Cl.
*A01H 5/00* (2006.01)

(52) U.S. Cl.
USPC ..... Plt./404

(58) Field of Classification Search
USPC ..... Plt./404
See application file for complete search history.

*Primary Examiner* — Annette Para
(74) *Attorney, Agent, or Firm* — Audrey Charles

(57) ABSTRACT

A new and distinct cultivar of *Angelonia* plant named 'Balangsparkl', characterized by its dark violet-colored flowers, medium green-colored foliage, and moderately vigorous, prostrate growth habit, is disclosed.

1 Drawing Sheet

Latin name of genus and species of plant claimed: *Angelonia angustifolia.*

Variety denomination: 'Balangsparkl'.

BACKGROUND OF THE INVENTION

The present invention relates to a new and distinct cultivar of *Angelonia* plant botanically known as *Angelonia angustifolia* and hereinafter referred to by the cultivar name 'Balangsparkl'.

The new cultivar originated in a controlled breeding program in Elburn, Ill. during April 2008. The objective of the breeding program was the development of *Angelonia* cultivars with unique flower coloration, continuous flowering, and a moderately vigorous, freely branching, and upright to prostrate growth habit The new *Angelonia* cultivar is the result of cross-pollination. The female (seed) parent of the new cultivar is the proprietary *Angelonia angustifolia* breeding selection coded 368-9-4-4, not patented, characterized by its dark pink-colored flowers, medium green-colored foliage, and vigorous, mounded growth habit. The male (pollen) parent of the new cultivar is the proprietary *Angelonia angustifolia* breeding selection coded 539-2, not patented, characterized by its medium purple-colored flowers, dark green-colored foliage, and moderately vigorous, prostrate growth habit. The new cultivar was discovered and selected as a single flowering plant within the progeny of the above stated cross-pollination during May 2009 in a controlled environment in Elburn, Ill.

Asexual reproduction of the new cultivar by terminal stem cuttings since May 2009 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balangsparkl' as a new and distinct cultivar of *Angelonia* plant:

1. Dark violet-colored flowers;
2. Medium green-colored foliage; and
3. Moderately vigorous, prostrate growth habit.

Plants of the new cultivar differ from plants of the female parent primarily in flower color, growth vigor and habit. Plants of the new cultivar differ from plants of the male parent primarily in having a darker flower color shade.

Of the many commercially available *Angelonia* cultivars, the most similar in comparison to the new cultivar is Carita Cascade Deep Purple 'Cartbas Depur' U.S. Plant Pat. No. 16,728. However, in side by side comparisons, plants of the new cultivar differ from plants of 'Cartbas Depur' in at least the following characteristics:

1. Plants of the new cultivar are shorter than plants of 'Cartbas Depur'; and
2. Plants of the new cultivar have shorter internode length than plants of 'Cartbas Depur'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balangsparkl'. The plants were grown in 4-inch pots for 7 weeks in a greenhouse in West Chicago, Ill. Plants were given one pinch at transplant.

DETAILED BOTANICAL DESCRIPTION

Figure 1:
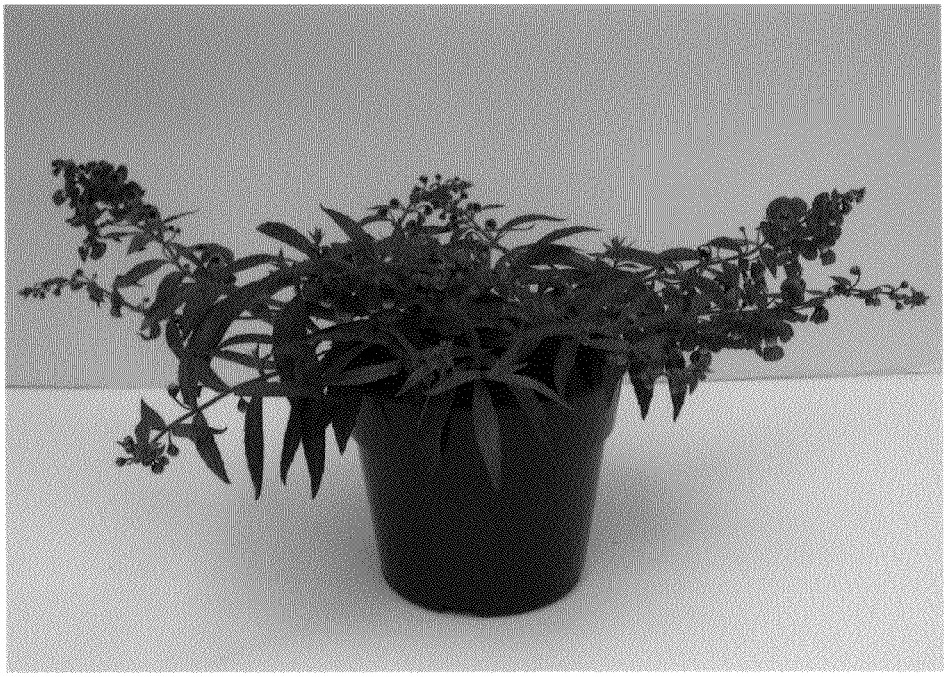
FIG. 1 illustrates a side view of the overall growth and flowering habit of 'Balangsparkl'.
Figure 2:
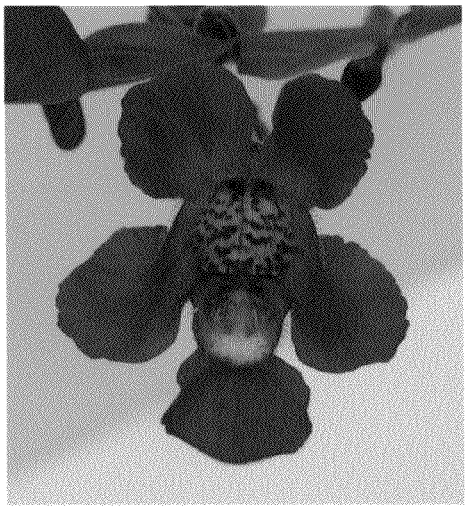
FIG. 2 illustrates a close-up view of an individual flower of 'Balangsparkl'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2013 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 7 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Angelonia angustifolia* cultivar Balangsparkl.

Parentage:

*Female parent*.—Proprietary Angelonia angustifolia breeding selection coded 368-9-4-4, not patented.

*Male parent*.—Proprietary Angelonia angustifolia breeding selection coded 539-2, not patented.

Propagation:

*Type cutting*.—Terminal stem.

*Time to initiate roots*.—Approximately 7 to 9 days.

*Time to produce a rooted cutting*.—Approximately 24 to 28 days.

*Root description*.—Fine, fibrous.

*Rooting habit*.—Freely branching.

Plant description:

*Commercial crop time*.—Approximately 5 to 8 weeks from a rooted cutting to finish in a 10 cm pot.

*Growth habit and general appearance*.—Moderately vigorous, prostrate.

*Size*.—Height from soil level to top of plant plane: Approximately 4.5 cm. Width: Approximately 36.1 cm.

*Branching habit*.—Freely branching, pinching enhances basal branching. Quantity of main branches per plant: Approximately 4.

*Branch*.—Shape: Square in cross section. Strength: Somewhat brittle. Length: Approximately 19.1 cm. Diameter: Approximately 3.0 mm. Length of central internode: Approximately 1.2 cm. Texture: Densely glandular pubescent. Gland color: 154D. Color of young stem: 146B with an overlay of 187A. Color of mature stem: 146A with an overlay of 187A.

Foliage description:

*General description*.—Quantity of leaves per main branch: Approximately 20. Fragrance: None. Form: Simple. Arrangement: Opposite.

*Leaves*.—Aspect: Perpendicular or obtuse angle to stem. Shape: Elliptic. Margin: Widely serrate. Apex: Acute. Base: Sessile. Venation pattern: Pinnate. Length of mature leaf: Approximately 6.2 cm. Width of mature leaf: Approximately 1.1 cm. Texture of upper surface: Glabrous. Texture of lower surface: Sparsely glandular pubescent on venation. Gland color: 154D. Color of upper surface of young foliage: 137A with indistinguishable venation. Color of lower surface of young and mature foliage: 137B with 146C for midvein only, other venation indistinguishable. Color of upper surface of mature foliage: Darker than 137A with indistinguishable venation.

Flowering description:

*Flowering habit*.—'Balangsparkl' is freely flowering under outdoor growing conditions with substantially continuous blooming from spring through autumn and year-round in greenhouse environment.

*Lastingness of individual flower on the plant*.—Approximately 7 to 10 days.

Inflorescence description:

*General description*.—Type: Terminal raceme. Quantity per plant: Approximately 4. Fragrance: Slight, sweet. Length or height: Approximately 13.3 cm. Width: Approximately 4.3 cm. Quantity of fully open flowers per inflorescence: Approximately 8.

Flower description:

*Type*.—Solitary, zygomorphic.

*Bud*.—Rate of opening: Generally takes 3 to 4 days for bud to progress from first color to fully open flower.

*Bud just before opening*.—Shape: Globular. Length: Approximately 6.0 mm. Diameter: Approximately 6.0 mm. Color of upper surface: 86B. Color of lower surface: 144B.

*Corolla*.—Shape: Bilabiate. Aspect: Facing outward. Length: Approximately 2.4 cm. Width: Approximately 2.0 cm. Depth: Approximately 1.0 cm.

*Petals*.—Quantity: 5 petals fused at base forming a throat and consisting of an upper lip with 2 petals and a lower lip with 3 petals, consisting of 2 lateral petals and one central petal. Shape: Obovate. Margin: Entire. Apex: Obtuse.

*Upper lip*.—Length of petals from throat: Approximately 7.0 mm. Width of each petal: Approximately 1.0 cm. Texture of upper surface: Sparsely glandular pubescent. Gland color: Colorless, transparent. Texture of lower surface: Glabrous. Color of upper surface when fully open: Between 86A and 86B. Color of lower surface when fully open: 86B.

*Lower lip, lateral petals*.—Length of petals from throat: Approximately 9.0 mm. Width of each petal: Approximately 9.0 mm. Texture of upper surface: Sparsely glandular pubescent. Texture of lower surface: Densely glandular pubescent. Gland color: Colorless, transparent. Color of upper surface when fully open: Between 86A and 86B. Color of lower surface when fully open: 86B.

*Lower lip, central petal*.—Length from the palate: Approximately 9.0 mm. Width: Approximately 1.0 cm. Texture of upper surface: Sparsely glandular pubescent. Texture of lower surface: Densely glandular pubescent. Gland color: Colorless, transparent. Color of upper surface when fully open: Between 86A and 86B. Color of lower surface when fully open: 86B.

*Throat*.—Length: Approximately 1.0 cm. Width: Approximately 7.0 mm. Texture of inner surface: Sparsely glandular pubescent. Gland color: Colorless, transparent. Texture of outer surface: Glabrous. Color of inner surface: NN155A with spots of N79A and N186A. Color of outer surface: NN155A with spots of N186A. Palate color: 145D with spots of N79A. Palate texture: Sparsely glandular pubescent. Gland color: Colorless, transparent. Teeth color: 145D.

*Calyx*.—Shape: Star, cupped. Diameter: Approximately 6.0 mm.

*Sepals*.—Quantity per flower: 5, fused at base. Shape: Lanceolate. Apex: Acute. Length: Approximately 4.0 mm. Width: Approximately 2.0 mm. Texture of upper surface: Glabrous. Texture of lower surface: Sparsely glandular pubescent. Gland color: Colorless, transparent. Color of upper surface: 146A with 187A at margin. Color of lower surface: 146A with an overlay of 187A.

*Pedicel*.—Strength: Strong, flexible. Aspect: Acute angle to stem becoming perpendicular from stem with age. Length: Approximately 1.3 cm. Diameter: Approximately 1.0 mm. Texture: Sparsely glandular pubescent. Gland color: 154D. Color: 146A with a heavy overlay of 187A.

*Reproductive organs*.—Androecium: Stamen quantity: 4. Filament length: Approximately 4.0 mm. Filament color: 145D with an overlay of 86D. Anther shape: Bilobed. Anther length: Approximately 1.0 mm. Anther color: 86A. Pollen amount: Abundant. Pollen color: NN155D. Gynoecium: Pistil quantity: 1 per flower. Pistil length: Approximately 5.0 mm. Stigma shape: Pointed. Stigma length: Less than 1 mm. Stigma color: Colorless, opaque. Style length: Approximately 4.0 mm. Style color: NN155D. Ovary diameter: Approximately 1.0 mm. Ovary texture: Glabrous. Ovary color: 145B dotted with 187A.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangsparkl', substantially as herein shown and described.

* * * * *